(12) United States Patent
Phan

(10) Patent No.: US 11,016,077 B2
(45) Date of Patent: May 25, 2021

(54) ANALYSIS APPARATUS

(71) Applicant: TOYOTA JIDOSHA KABUSHIKI KAISHA, Aichi (JP)

(72) Inventor: Long Vinh Phan, Aichi-ken (JP)

(73) Assignee: TOYOTA JIDOSHA KABUSHIKI KAISHA, Aichi-Ken (JP)

( * ) Notice: Subject to any disclaimer, the term of this patent is extended or adjusted under 35 U.S.C. 154(b) by 155 days.

(21) Appl. No.: 16/351,515

(22) Filed: Mar. 13, 2019

(65) Prior Publication Data
US 2019/0285610 A1    Sep. 19, 2019

(30) Foreign Application Priority Data
Mar. 14, 2018   (JP) .............................. JP2018-046636

(51) Int. Cl.
*G01N 33/44* (2006.01)
*G01N 11/10* (2006.01)
*G01L 1/04* (2006.01)

(52) U.S. Cl.
CPC .............. *G01N 33/445* (2013.01); *G01L 1/04* (2013.01); *G01N 11/10* (2013.01)

(58) Field of Classification Search
CPC ............................ G01N 33/445; G01N 11/10
USPC ........................................................ 73/54.37
See application file for complete search history.

(56) References Cited

FOREIGN PATENT DOCUMENTS

JP        2015-75383 A     4/2015

*Primary Examiner* — John Fitzgerald
*Assistant Examiner* — Rodney T Frank
(74) *Attorney, Agent, or Firm* — Hauptman Ham, LLP

(57) ABSTRACT

Provided is an analysis apparatus configured to analyze characteristics of a viscoelastic material based on a viscoelastic material constitutive law in which an elastic element and a viscoelastic element are arranged in parallel with each other; calculate, in a viscoelastic material model divided into a finite number of elements each having a node, a displacement amount of the node; calculate a strain rate at the node through use of the displacement amount; calculate, as a relaxation time of the viscoelastic element, a value proportional to a value of a power using the strain rate as a base and a value of a power using a shift factor of a temperature-time conversion law as a base; and calculate a stress at the node through use of the relaxation time.

12 Claims, 10 Drawing Sheets

-- PRIOR ART --

# ANALYSIS APPARATUS

CLAIM OF PRIORITY

The present application claims priority from Japanese patent application JP 201846636 filed on Mar. 14, 2018, the content of which is hereby incorporated by reference into this application.

BACKGROUND

1. Technical Field

The present disclosure relates to an analysis apparatus configured to analyze characteristics of a viscoelastic material by a finite element method.

2. Description of the Related Art

A viscoelastic material constitutive law in which an elastic element and a viscoelastic element are arranged in parallel with each other has heretofore been known as a model for analyzing the characteristics of a viscoelastic material (e.g., rubber).

One apparatus of the related art (hereinafter referred to as "related-art apparatus") is configured to analyze the stress-strain characteristics of the viscoelastic material by using a relaxation time representing the damping characteristics of the viscoelastic element as a constant (e.g., Japanese Patent No. 6048358).

The behavior of the viscoelastic material may vary depending on an environmental temperature. However, in the related-art apparatus, the relaxation time is defined as a function that is independent of the environmental temperature. Therefore, the related-art apparatus cannot analyze the characteristics (e.g., stress-strain characteristics) of the viscoelastic material in consideration of the dependence of the viscoelastic material on the environmental temperature.

SUMMARY

The present disclosure provides an analysis apparatus capable of reproducing the dependence of a viscoelastic material on an environmental temperature.

An analysis apparatus according to one embodiment is an apparatus configured to analyze characteristics of a viscoelastic material based on a viscoelastic material constitutive law in which an elastic element and a viscoelastic element are arranged in parallel with each other.

The analysis apparatus includes: a first calculation module (1041) configured to set a predetermined input condition for a viscoelastic material model divided into a finite number of elements each having a node to calculate a displacement amount of the node; a second calculation module (1042) configured to calculate a strain rate at the node through use of the displacement amount; a third calculation module (1043) configured to calculate, as a relaxation time ($\tau_i$) of the viscoelastic element, a value proportional to a value of a power using the strain rate as a base and a value of a power using a shift factor ($\alpha(T)$) of a temperature-time conversion law as a base; and a fourth calculation module (1044) configured to calculate a stress at the node through use of the relaxation time.

In the analysis apparatus having such configuration, the relaxation time representing damping characteristics of the viscoelastic element is calculated by using a power function of the shift factor of the temperature-time conversion law. Therefore, the analysis apparatus can reproduce the dependence of a viscoelastic material on an environmental temperature. Thus, the accuracy with which the characteristics (e.g., stress-strain characteristics) of the viscoelastic material are predicted when the environmental temperature has changed can be improved.

In one aspect of the analysis apparatus, the analysis apparatus further includes a shift factor calculation module (1030) configured to calculate the shift factor. The shift factor calculation module is configured to: calculate, from test results of a harmonic oscillation test performed at a plurality of environmental temperatures by using the viscoelastic material serving as an analysis object, an elastic modulus of the viscoelastic material at each of the plurality of environmental temperatures; normalize the elastic modulus at each of the plurality of environmental temperatures through use of a reference elastic modulus ($G(T_0)$) at a reference temperature ($T_0$) out of the plurality of environmental temperatures; determine a function f(T) representing a relationship between a logarithmic value of the normalized elastic modulus and a temperature; and calculate a shift factor $\alpha(T)$ based on a material constant $m_i$ obtained from a relationship between an elastic modulus and an amplitude in the harmonic oscillation test in which the viscoelastic material is used, the function f(T), and the following expression (A).

$$f(T)=(1+m_i)\log \alpha(T) \tag{A}$$

According to this aspect, the shift factor of the temperature-time conversion law can be calculated from the test results of the harmonic oscillation test performed at the plurality of environmental temperatures.

In one aspect of the analysis apparatus, the analysis apparatus further includes a shift factor calculation module (1030) configured to calculate the shift factor. The shift factor calculation module is configured to: produce, from test results of a stress relaxation test performed at a plurality of environmental temperatures by using the viscoelastic material serving as an analysis object, a stress relaxation graph for each of the plurality of environmental temperatures; normalize the stress relaxation graph for each of the plurality of environmental temperatures through use of a maximum stress ($\sigma_0$) at a reference temperature ($T_0$) out of the plurality of environmental temperatures to calculate a relaxation time at each of the plurality of environmental temperatures; normalize a logarithmic value of the relaxation time at each of the plurality of environmental temperatures through use of a relaxation time at the reference temperature to determine a function f(T) representing a relationship between the normalized logarithmic value of the relaxation time and a temperature; and calculate a shift factor $\alpha(T)$ based on a material constant $m_i$ obtained from a relationship between an elastic modulus and an amplitude in a harmonic oscillation test in which the viscoelastic material is used, the function f(T), and the following expression (B).

$$f(T)=(1+m_i)\log \alpha(T) \tag{B}$$

According to this aspect, the shift factor of the temperature-time conversion law can be calculated from the test results of the stress relaxation test performed at the plurality of environmental temperatures.

In one aspect of the analysis apparatus, an exponent of the value of the power using the shift factor as a base is a value obtained by adding 1 to an exponent of the value of the power using the strain rate as a base.

In the above description, in order to facilitate understanding of the above one or more aspect of the apparatus, a name and/or reference numeral used in one or more embodiments described later are enclosed in parentheses and assigned to each of the constituent features of the apparatus. However, each of the constituent features of the apparatus is not limited to the embodiments defined by the name and/or reference numeral.

DESCRIPTION OF THE EMBODIMENTS

Now, referring to the accompanying drawings, a description is given of one or more embodiments of the present disclosure. The accompanying drawings are illustrations of the embodiments, but those illustrations are examples to be used for the understanding of the embodiments, and are not to be used to limit the interpretation of the disclosure.

<Outline of Analysis Involving Using Viscoelastic Material Constitutive Law>

Figure 1:
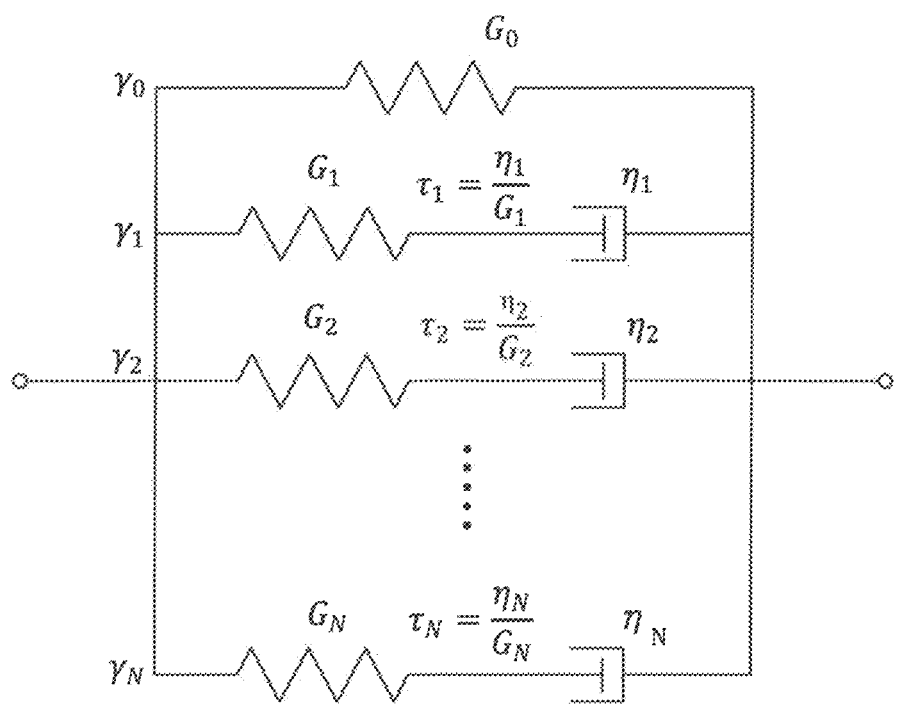
FIG. 1 is a view for schematically illustrating a viscoelastic material constitutive law.

A viscoelastic material constitutive law to be used in an embodiment is described with reference to FIG. 1. In a viscoelastic material model illustrated in FIG. 1, an elastic element having an elastic modulus $G_0$ and a plurality of viscoelastic elements are connected in parallel with each other. Each of the plurality of viscoelastic elements has an elastic element having an elastic modulus $G_i$ (i=1 to N, N represents a natural number) and a viscous element having a viscosity coefficient which is connected in series to the elastic element. The model in which the elastic element and the viscoelastic elements are combined with each other is used as a model for representing the characteristics of rubber parts, such as a tire and a rubber bush.

Here, a rigidity ratio in each of the elastic element and the viscoelastic elements to be connected in parallel with each other is represented by $\gamma_i$ (i=0 to N), and a relaxation time in each of the viscoelastic elements is represented by $\tau_i = \eta_i/G_i$. A stress S at a time t in the viscoelastic material model is represented by the following expression (1) and expression (2).

$$S(t) = S^\circ(t) - J^{-\frac{2}{3}} DEV\left[\sum_{i=1}^{N} Qi(t)\right] \quad (1)$$

$$\frac{dQ_i}{dt} + \frac{1}{\tau_i}Q_i = \frac{\gamma_i}{\tau_i} DEV\left[2\frac{\partial \overline{W}^\circ(\overline{C})}{\partial \overline{C}}\right] \quad (2)$$

In the expression (1), S represents a second Piola-Kirchhoff stress, and $S^\circ$ having a superscript represents the stress of only an elastic component from which a viscous force component has been removed. J represents the volume change ratio of a viscoelastic material. The volume change ratio J is represented by J=det[F] through the use of the determinant (det) of a deformation gradient tensor F representing a linear transformation relationship between positions before deformation and after the deformation at a certain substance point. An operator DEV is represented by the following expression (3) through the use of a right Cauchy-Green tensor $C=F^T \cdot F$. [●] in the expression (3) represents a variable serving as the operand of the operator DEV.

$$DEV[●]=[●]-1/3[(●):C]\cdot C^{-1} \quad (3)$$

$Q_i$ in the expression (1) represents a viscous force in each of the viscoelastic elements. $Q_i$ is represented by an evolution equation represented by the expression (2).

$\overline{W}^\circ$ represents the deviator of strain potential energy in a superelastic body.

$\overline{C}$ represents a modified right Cauchy-Green tensor from which a volume component has been removed, and is represented by the following expression (4).

$$\overline{C}=J^{-2/3}C \quad (4)$$

The second Piola-Kirchhoff stress S represented by the expression (1) and the expression (2) can be represented in an integral form represented by the following expression (5).

$$S(t) = JU^{\sigma'}C^{-1}(t) + J^{-2/3}\int_{-\infty}^{t} g(t-s)\frac{d}{ds}\left[DEV\left[2\frac{\partial \overline{W}^\circ(\overline{C})}{\partial \overline{C}}\right]\right]ds \quad (5)$$

$$g(t) = \gamma_0 + \sum_{i=1}^{N} \gamma_i \exp(-t/\tau_i) \quad (6)$$

$U^o$
represents the volume component of the strain potential energy. Further, g(t) represents a relaxation function, and is represented by the expression (6).

Here, the deformation of the expression (5) represented as a function of the time t into the following expression (7) can provide a second Piola-Kirchhoff stress $S_{n+1}$ at a time $t_{n+1}$. A function in a calculation step n is represented by $(\bullet)_n$, and a function in a calculation step n+1 is represented by $(\bullet)_{n+1}$.

$$S_{n+1} = JU^{o'}(J_{n+1})C_{n+1}^{-1} + \quad (7)$$
$$\gamma_0 J_{n+1}^{-2/3} DEV_{n+1}\left[2\frac{\partial \overline{W}^o(\overline{C}_{n+1})}{\partial \overline{C}}\right] + \sum_{i=1}^{N} \gamma_i J_{n+1}^{-2/3} DEV_{n+1}[H_{n+1}^{(i)}]$$

$H^{(i)}_{n+1}$ in the expression (7) represents an intermediate function obtained as an approximate solution by integration over a time interval $[t_n, t_{n+1}]$ through the use of a midpoint rule, and is represented by the following expression (8).

$$H_{n+1}^{(i)} = H_n^{(i)}\exp\left[-\frac{\Delta t_n}{\tau_i}\right] - (\tilde{S}_{n+1}^o - \tilde{S}_n^o)\exp\left[-\frac{\Delta t_n}{2\tau_i}\right] \quad (8)$$

$\tilde{S}_{n+1}^o, \tilde{S}_n^o$
are defined by the following expression (9) and expression (10), respectively.

$$\tilde{S}_{n+1}^o = DEV_{n+1}\left[2\frac{\partial \overline{W}^o(\overline{C}_{n+1})}{\partial \overline{C}}\right] \quad (9)$$

$$\tilde{S}_n^o = DEV_n\left[2\frac{\partial \overline{W}^o(\overline{C}_n)}{\partial \overline{C}}\right] \quad (10)$$

A Kirchhoff elastic stress
$\bar{\tau}_{n+1}^o$
is defined by the following expression (11).

$$\bar{\tau}_{n+1}^o = dev\left[2\overline{F}_{n+1}\frac{\partial \overline{W}^o(\overline{C}_{n+1})}{\partial \overline{C}}\overline{F}_{n+1}^T\right] \quad (11)$$

Thus, the expression (9) can also be represented by the following expression (12).

$$\tilde{S}_{n+1}^o = \overline{F}_{n+1}^{-1}\bar{\tau}_{n+1}^o \overline{F}_{n+1}^{-T} \quad (12)$$

Further, a Kirchhoff stress tensor $T_{n+1}$ can be represented by the following expression (13) through the use of the second Piola-Kirchhoff stress $S_{n+1}$.

$$\tau_{n+1} = F_{n+1}S_{n+1}F_{n+1}^T \quad (13)$$

Therefore, as can be seen from the expression (7) and the expression (13), the Kirchhoff stress tensor can be represented by the following expression (14).

$$\tau_{n+1} = JU^{o'}(J_{n+1})I + g^*(\Delta t_n)\bar{\tau}_{n+1}^o + \sum_{i=1}^{N} \gamma_i dev\left[\overline{F}_{n+1}H_{n+1}^{(i)}\overline{F}_{n+1}^T\right] \quad (14)$$

An operator dev in the expression (14) is defined by the following expression (15). (●) in the expression (15) represents a variable serving as the operand of the operator DEV.

$$dev[\overline{F}_{n+1}(\bullet)\overline{F}_{n+1}^T] = J_{n+1}^{2/3}\overline{F}_{n+1}[DEV_{n+1}(\bullet)]\overline{F}_{n+1}^T \quad (15)$$

Further, a relaxation function g* in the expression (14) is defined by the following expression (16).

$$g^*(\Delta t_n) = \gamma_0 + \sum_{i=1}^{N} \gamma_i \exp(-\Delta t_n/2\tau_i) \quad (16)$$

As can be seen from the foregoing, the value of the Kirchhoff stress tensor can be obtained by holding the $H^{(i)}_{n+1}$ and
$\tilde{S}_{n+1}^o$
as intermediate functions for each calculation step.

<Analysis Processing>

In the viscoelastic model of the related-art apparatus, the relaxation time $\tau_i$ has been defined as a function that is independent of an environmental temperature. Therefore, there has been a problem in that the accuracy with which the characteristics (e.g., stress-strain characteristics) of a viscoelastic material are predicted when the environmental temperature has changed is not high.

In view of the foregoing, the inventors of the present application have found the definition of the relaxation time $\tau_i$ as a power function of the shift factor of a temperature-time conversion law (temperature-time superposition principle). Thus, the dependence of the viscoelastic material on the environmental temperature is reproduced, and hence the accuracy with which the characteristics (e.g., stress-strain characteristics) of the viscoelastic material are predicted can be improved.

In this embodiment the relaxation time $\tau_i$ satisfying a relational equation represented by the following expression (17) is used.

$$\tau_i = A_i \alpha(T)^{m_i+1} \|\overline{E}'\|^{m_i} \quad (17)$$

$\overline{E}$
represents a Green-Lagrange strain tensor from which a deviator has been removed, and is represented by the following expression (18) through the use of the following modified right Cauchy-Green tensor:
$\overline{C}$ $$\overline{E} = 1/2(\overline{C}-1) \quad (18)$$

$\overline{E}'$
represents a strain rate, and represents the time derivative of the strain tensor.

$\|\overline{E}'\|$
represents the magnitude of the strain rate, and is represented by the following expression (19) when a three-dimensional strain tensor is used.

$$\|\overline{E}'\| = \sqrt{\sum_{j=1}^{3}\sum_{k=1}^{3}(\overline{E}'_{jk})^2} \quad (19)$$

α(T) is a value to be newly introduced in this embodiment, and represents the shift factor of the temperature-time conversion law. T represents the environmental temperature. $A_i$ and $m_i$ each represent a material constant. Therefore, as represented by the expression (17), the relaxation time $\tau_i$ is defined as a value proportional to the value of a power using the strain rate as a base and the value of a power using the shift factor of the temperature-time conversion law as a base. Further, the exponent of the value of the power using the shift factor of the temperature-time conversion law as a base is a value obtained by adding 1 to the exponent of the value of the power using the strain rate as a base.

A method of calculating the shift factor α(T) is described later. Further, methods of calculating the material constants $A_i$ and $m_i$ are also described later.

Next, expression deformation required in terms of numerical analysis at the time of the introduction of the relaxation time $\tau_i$ represented by the expression (17) is described. In order to calculate the Kirchhoff stress by using the expression (14), an expression including the relaxation time $\tau_i$ is required to be deformed. Specifically, the expression (8) is deformed into the following expression (20).

$$H_{n+1}^{(i)} = \tilde{H}_n^{(i)} + \overline{S}_{n+1}^o \exp\left[-\frac{\Delta t_n}{2\tau_i\left(\alpha\left(\frac{T_n+T_{n+1}}{2}\right),\left\|\frac{\overline{E}_{n+1}'+\overline{E}_n'}{2}\right\|\right)}\right] \quad (20)$$

$$\tilde{H}_n^{(i)} = H_n^{(i)}\exp\left[-\frac{\Delta t_n}{\tau_i(\alpha(T_n),\|\overline{E}_n'\|)}\right] - \quad (21)$$

$$\overline{S}_n^o \exp\left[-\frac{\Delta t_n}{2\tau_i\left(\alpha\left(\frac{T_n+T_{n+1}}{2}\right),\left\|\frac{\overline{E}_{n+1}'+\overline{E}_n'}{2}\right\|\right)}\right]$$

Further, the expression (16) is deformed into the following expression (22).

$$g^*(\Delta t_n) = \gamma_\infty + \sum_{i=1}^N \gamma_i \exp\left[-\frac{\Delta t_n}{2\tau_i\left(\alpha\left(\frac{T_n+T_{n+1}}{2}\right),\left\|\frac{\overline{E}_{n+1}'+\overline{E}_n'}{2}\right\|\right)}\right] \quad (22)$$

Here, a function of the relaxation time $\tau_i$ is defined by the following expression (23) and expression (24).

$$\tau_i(\alpha(T_n),\|\overline{E}_n'\|) = A_i\alpha(T_n)^{m_i+1}\|\overline{E}_n'\|^{m_i} \quad (23)$$

$$\tau_i\left(\alpha\left(\frac{T_n+T_{n+1}}{2}\right),\left\|\frac{\overline{E}_{n+1}'+\overline{E}_n'}{2}\right\|\right) = A_i\alpha\left(\frac{T_n+T_{n+1}}{2}\right)^{m_i+1}\left\|\frac{\overline{E}_{n+1}'+\overline{E}_n'}{2}\right\|^{m_i} \quad (24)$$

The expression (24) is used as the relaxation time $\tau_i$ in each of the second term on the right side of the expression (20) and the second term on the right side of the expression (21), and the expression (22). This is because an approximate solution obtained by integration over the time interval $[t_n, t_{n+1}]$ through the use of the midpoint rule is used.

Next, methods of calculating the material constants $m_i$ and $A_i$ in the viscoelastic material model described in this embodiment are described.

Figure 2:
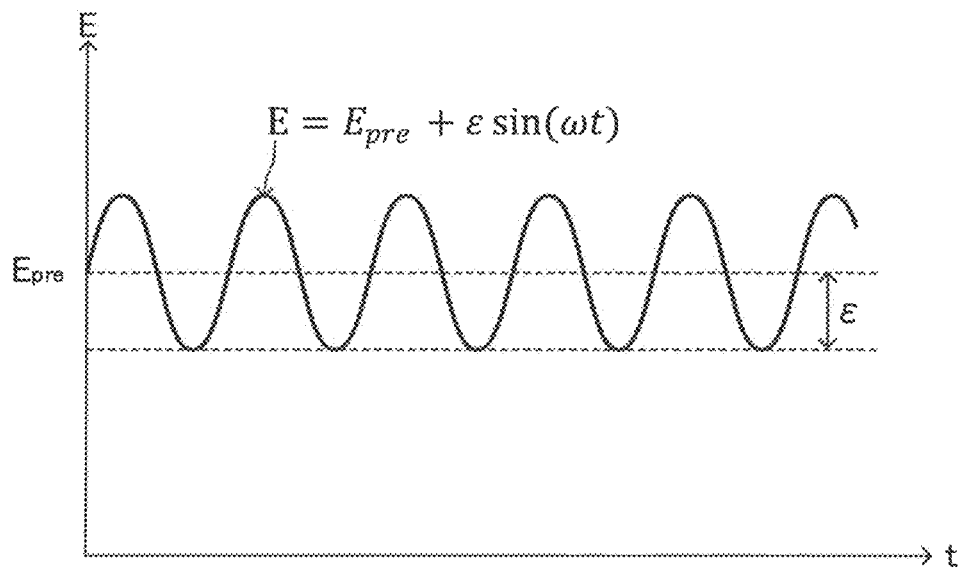
FIG. 2 is a graph for showing a test condition in a harmonic oscillation test.

FIG. 2 is a graph for showing a test condition in a harmonic oscillation test. In FIG. 2, a graph of a strain $E = E_{pre} + \varepsilon \sin(\omega t)$ to be applied to a test body of a viscoelastic material when a prestrain is represented by $E_{pre}$, an amplitude is represented by ε, and a frequency is represented by ω is shown by using an axis of abscissa indicating the time t. A dynamic elastic modulus G of the test body at a time when such strain E is applied is measured. Then, the material constant $m_i$ can be derived by using a relationship represented by the following expression (25).

$$\|G(t)\| \propto \varepsilon^{-m_i-1} \quad (25)$$

Here, the expression (2) is deformed into an evolution equation represented by the following expression (26) by substituting the expression (17) into the expression (2). The expression (25) is obtained by solving the expression (26).

$$\frac{dQ_i}{dt} + \frac{1}{A_i\alpha(T)^{m_i+1}\|\overline{E}'\|^{m_i}}Q_i = \frac{\gamma_i}{A_i\alpha(T)^{m_i+1}\|\overline{E}'\|^{m_i}}DEV\left[2\frac{\partial \overline{W}^o(\overline{C})}{\partial \overline{C}}\right] \quad (26)$$

Figure 3:
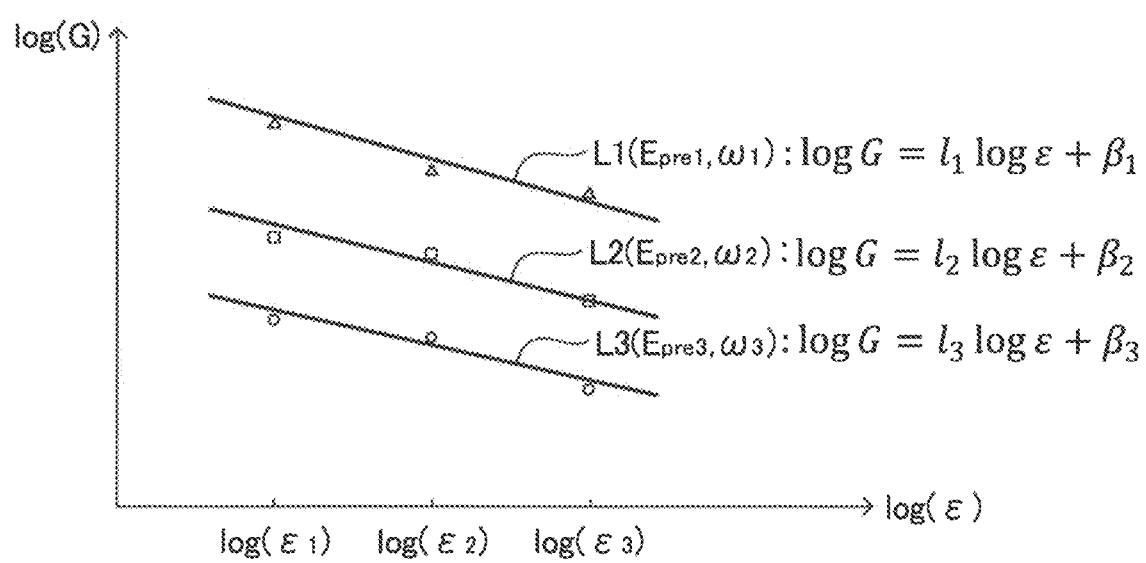
FIG. 3 is a graph for schematically showing a method of calculating a material constant $m_i$.

FIG. 3 is a graph for schematically showing the method of calculating the material constant $m_i$. In FIG. 3, a logarithmic value log(G) of the dynamic elastic modulus G serving as a test result value when the prestrain $E_{pre}$ and the frequency ω are changed is plotted against an axis of abscissa indicating a logarithmic value log(ε) of the amplitude ε to be applied in the harmonic oscillation test. An approximate line L1 on the graph is an approximate line having a gradient $I_1$, the line corresponding to plotted values at a time when values $\varepsilon_1$ to $\varepsilon_3$ of the amplitude are changed with respect to a prestrain $E_{pre1}$ and a frequency $\omega_1$. Similarly, an approximate line L2 is an approximate line having a gradient $I_2$, the line corresponding to plotted values at a time when the values $\varepsilon_1$ to $\varepsilon_3$ of the amplitude are changed with respect to a prestrain $E_{pre2}$ and a frequency $\omega_2$. An approximate line L3 is an approximate line having a gradient $I_3$, the line corresponding to plotted values at a time when the values $\varepsilon_1$ to $\varepsilon_3$ of the amplitude are changed with respect to a prestrain $E_{pre3}$ and a frequency $\omega_3$. The following expression (27) can be obtained by taking the logarithms of both sides of the expression (25). Therefore, the material constant $m_i$ can be obtained from the gradient $I_i$.

$$\log G = (-1-m_i) \times \log \varepsilon + \beta \quad (27)$$

As can be seen from the expression (27), the material constant $m_i$ can be obtained from the following relational equation ($m_i = -1 - I_i$). β in the expression (27) represents the intercept of an approximate line shown in FIG. 3. Thus, the material constant $m_i$ corresponding to an applied frequency $\omega_i$ in the harmonic oscillation test can be obtained. The values of the amplitude ε shown in FIG. 3 are examples. Two values may be used as the amplitude ε, or four or more values may be used as the amplitude ε.

When the value of the material constant $m_i$ does not change with the applied frequency $\omega_i$ to a very large extent, instead of obtaining the material constant $m_i$ corresponding to each frequency, a common exponent m obtained as the average of the respective material constants $m_i$ may be used. In the case where the common exponent m is used, a calculation load can be reduced as compared to that of the case where the different material constants $m_i$ are used for the respective frequencies.

The material constant $A_i$ can be obtained from a relationship represented by the following expression (28) by using the material constant $m_i$ obtained by the above-mentioned method. A frequency $\omega_i$ in the expression (28) is the applied frequency in the harmonic oscillation test. The material constants $A_i$ corresponding to the respective viscoelastic elements different from each other in frequency component $\omega_i$ can be obtained by changing the frequency.

$$A_i = \frac{\overline{\omega}_i}{(\overline{\omega}_i \varepsilon)^{-m_i}} \qquad (28)$$

Figure 4:
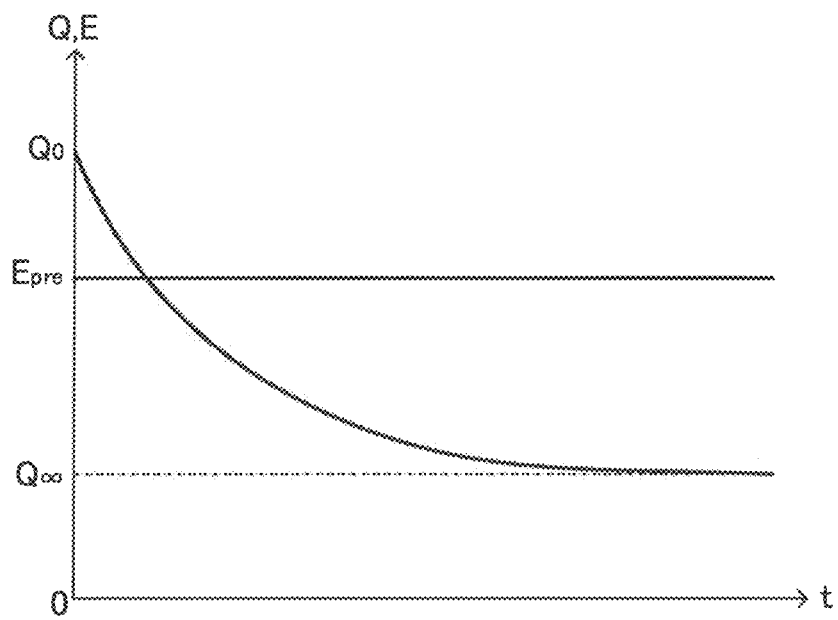
FIG. 4 is a graph for schematically showing a stress relaxation curve in a stress relaxation test.

Next, a method of calculating the rigidity ratio $\gamma_0$ of the elastic element is described. FIG. 4 is a graph for schematically showing a stress relaxation curve in a stress relaxation test. In FIG. 4, the test result of the measurement of the change of a stress Q with time at a time when the input strain $E_{pre}$ is kept constant is shown. The rigidity ratio of the elastic element can be obtained from an instantaneous stress $Q_0$ at the time t=0 and a relaxation stress $Q_\infty$ at the time t=∞ shown in the test result by using the following relational equation ($\gamma_0 = Q_\infty / Q_0$).

Next, a method of calculating the elastic modulus $G_0$ of the elastic element is described. In this embodiment, the elastic modulus $G_0$ of the elastic element is determined by defining superelastic coefficients C10, C20, and C30 defined in a Yeoh material model serving as a superelastic material model. Those superelastic coefficients can be derived by obtaining the relaxation stresses $Q_\infty$ for the plurality of input strains $E_{pre}$ in the stress relaxation test shown in FIG. 4.

Figure 5:
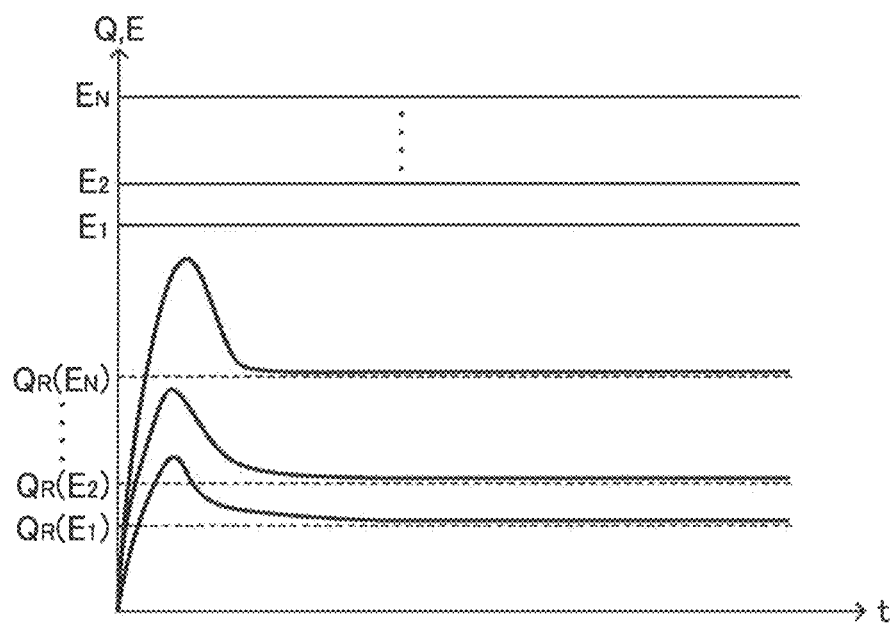
FIG. 5 is a graph for showing a stress relaxation curve at a time when an input strain is changed.
Figure 6:
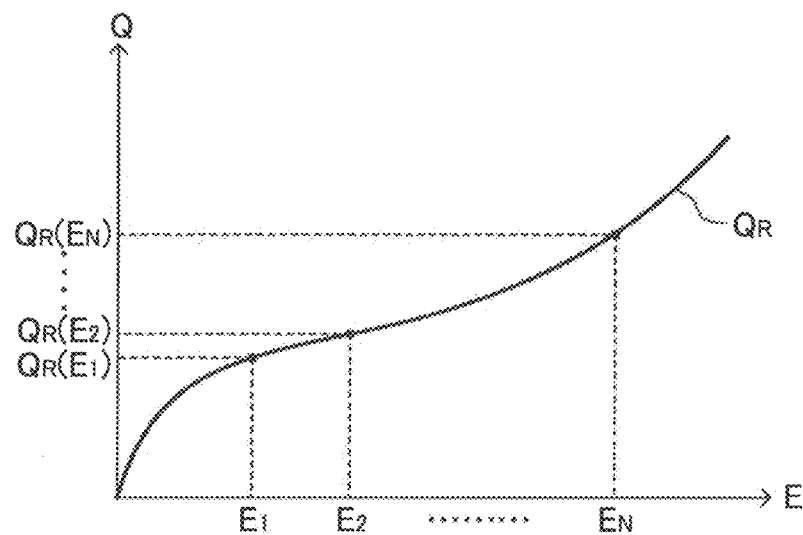
FIG. 6 is a graph for showing a static characteristic curve between a strain and a stress.

FIG. 5 is a graph for showing a stress relaxation curve at a time when an input strain $E_k$ (k=1 to N, N represents a natural number) is changed. FIG. 6 is a graph for showing a static characteristic curve $Q_R$ between the strain E and the stress Q. As shown in FIG. 5, a stress relaxation test is performed for each of the plurality of load strains $E_1$ to $E_N$ having different values to provide relaxation stresses $Q_R(E_1)$ to $Q_R(E_N)$ corresponding to the respective load strains $E_k$. The static characteristic curve $Q_R$ shown in FIG. 6 is obtained by graphically showing the relational equation between the load strain and the relaxation stress as a stress-strain curve. The elastic modulus $G_0$ of the elastic element can be determined by defining the superelastic coefficients C10, C20, and C30 that can approximate the static characteristic curve through use of a known technology.

Figure 7:
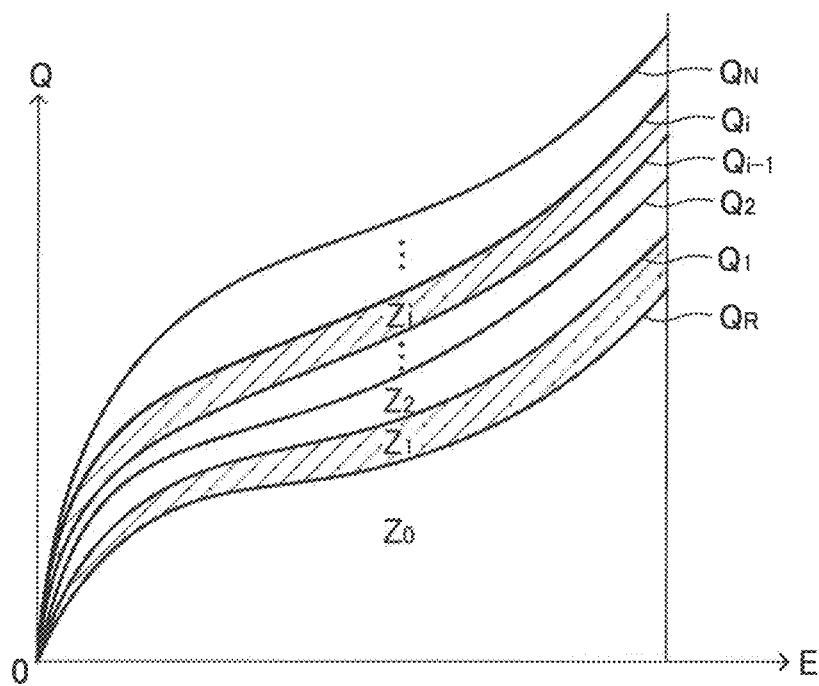
FIG. 7 is a graph for showing a relation curve and a static characteristic curve between a strain and a stress in a constant strain rate test.

Next, a method of calculating the rigidity ratio $\gamma_i$ of each of the viscoelastic elements is described. In FIG. 7, a relation curve $Q_i$ and a static characteristic curve $Q_R$ between the strain E and the stress Q in a constant strain rate test are shown. The static characteristic curve $Q_R$ is the same as the static characteristic curve shown in FIG. 6. The relation curves $Q_1$ to $Q_N$ represent the test results of the strain E and the stress Q corresponding to the case in which a strain rate $V_i$ is changed from $V_1$ to $V_N$ in the constant strain rate test. Here, an i-th relation curve $Q_i$ corresponds to the dynamic characteristics of an i-th viscoelastic element, and corresponds to the viscoelastic element having the material constant $A_i$ calculated from the applied frequency $\omega_i$. At this time, the strain rate $V_i$ satisfies the following relational equation; ($V_i = \omega_i \varepsilon$) based on the applied frequency $\omega_i$ and the amplitude $\varepsilon$ in the harmonic oscillation test.

The rigidity ratio $\gamma_i$ of each viscoelastic element can be obtained from an area $Z_i$ surrounded by the relation curve $Q_i$ between the strain E and the stress Q shown in FIG. 6. When an area surrounded by the static characteristic curve $Q_R$ is represented by $Z_0$, and an increase in area due to an increase from the (i-1)-th strain rate to the i-th strain rate is represented by $Z_i$, the rigidity ratio $\gamma_i$ can be calculated from the following relational equation ($\gamma_i = \gamma_0 \times Z_i / Z_0$).

The material constants $m_i$ and $A_i$, the rigidity ratios $\gamma_0$ and $\gamma_i$, and the elastic modulus $G_0$ can be identified by the foregoing methods.

Figure 8A:
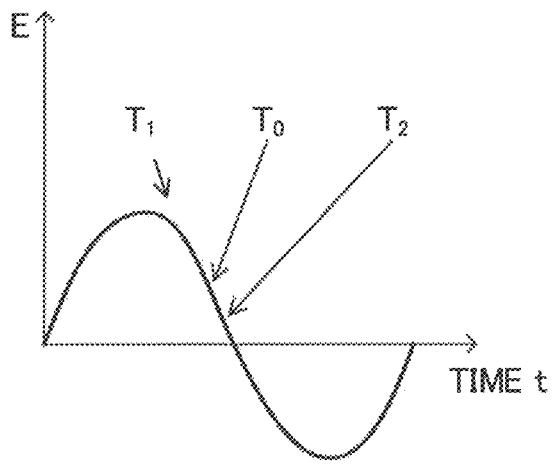
FIG. 8A and FIG. 8B are each a graph for showing the flow of the calculation of a shift factor $\alpha(T)$ of a temperature-time conversion law in an embodiment of the present disclosure.

Next, a method of calculating the shift factor $\alpha(T)$ of the temperature-time conversion law is described. As shown in FIG. 8A, the harmonic oscillation test is performed on the test body of the viscoelastic material at a plurality of environmental temperatures ($T = T_0, T_1, T_2, \ldots, T_N$). At this time, the amplitude $\varepsilon$ is constant and the prestrain is also constant.

Here, the following expression (29) is valid for a relationship between an elastic modulus G(T) and the shift factor $\alpha(T)$ in the harmonic oscillation test.

$$G(T) \sim \alpha(T)^{(-1-m_i)} \qquad (29)$$

Figure 8B:
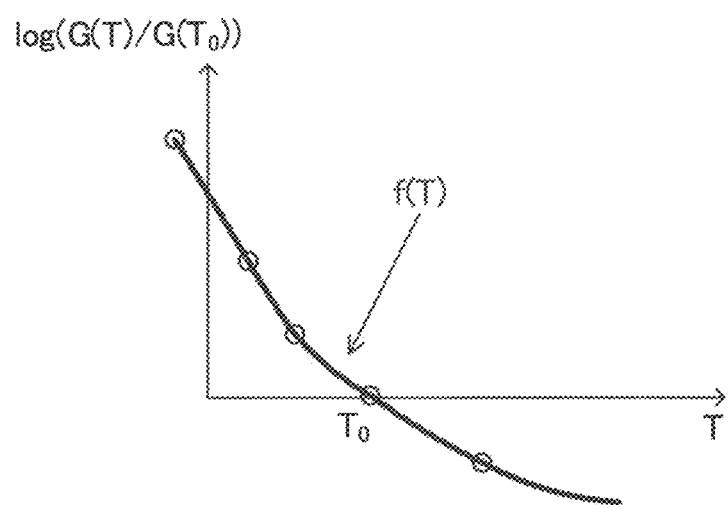

Therefore, first, the elastic modulus G(T) is calculated from the test results of the harmonic oscillation test. Here, the $T_0$ out of the plurality of environmental temperatures ($T_0, T_1, T_2, \ldots, T_N$) is used as a reference temperature. Each of elastic moduli at the plurality of environmental temperatures is normalized through the use of an elastic modulus $G(T_0)$ at the reference temperature $T_0$. Next, as shown in FIG. 8B, a scatter diagram in which a "logarithmic value $\log(G(T)/G(T_0))$ of the normalized elastic modulus" is plotted against an axis of abscissa indicating the temperature T is produced. Then, as shown in FIG. 8B, a regression function f(T) is determined by the method of least squares. The regression function f(T) may be any one of a regression line and a regression curve. Here, the following expression (30) is valid for a relationship between the determined function f(T) and the shift factor $\alpha(T)$.

$$f(T) = (1 + m_i) \log \alpha(T) \qquad (30)$$

Therefore, the shift factor $\alpha(T)$ can be calculated by using the material constant $m_i$.

<Hardware Configuration of Analysis Apparatus>

Figure 9:
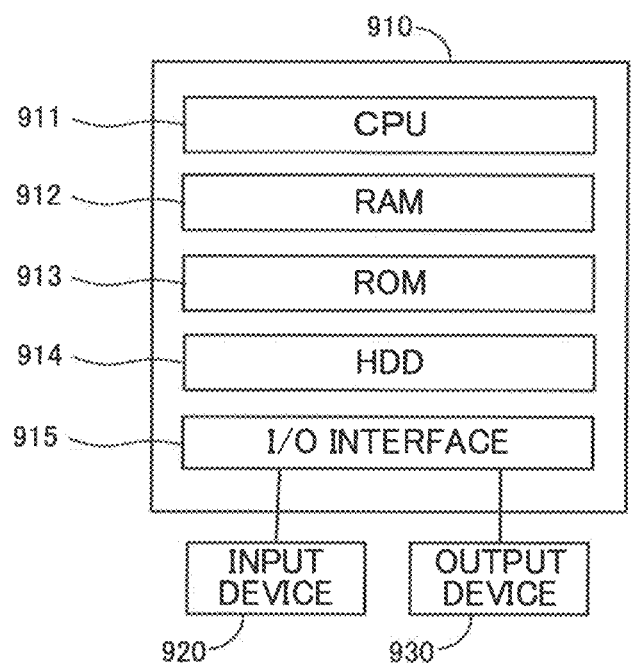
FIG. 9 is a block diagram for illustrating the hardware configuration of an analysis apparatus according to the embodiment of the present disclosure.

Next, an analysis apparatus configured to analyze the characteristics of a viscoelastic material by a finite element method is described. As illustrated in FIG. 9, the analysis apparatus includes an information processing device 910, an input device 920, and an output device 930.

The information processing device 910 includes a CPU 911, a RAM 912, a ROM 913, a hard disk drive (HDD) 914, and an I/O interface 915. The ROM 913 stores an instruction (a program or a routine) to be executed by the CPU 911. The CPU 911 is configured to execute the instruction to achieve various functions to be described later.

The information processing device 910 is connected to the input device 920 and the output device 930 via the I/O interface 915. The input device 920 is a device configured to receive various requests from a user, and includes a keyboard and a mouse. The output device 930 includes a display configured to output a result of processing executed by the information processing device 910.

<Function Configuration of Analysis Apparatus>

Figure 10:
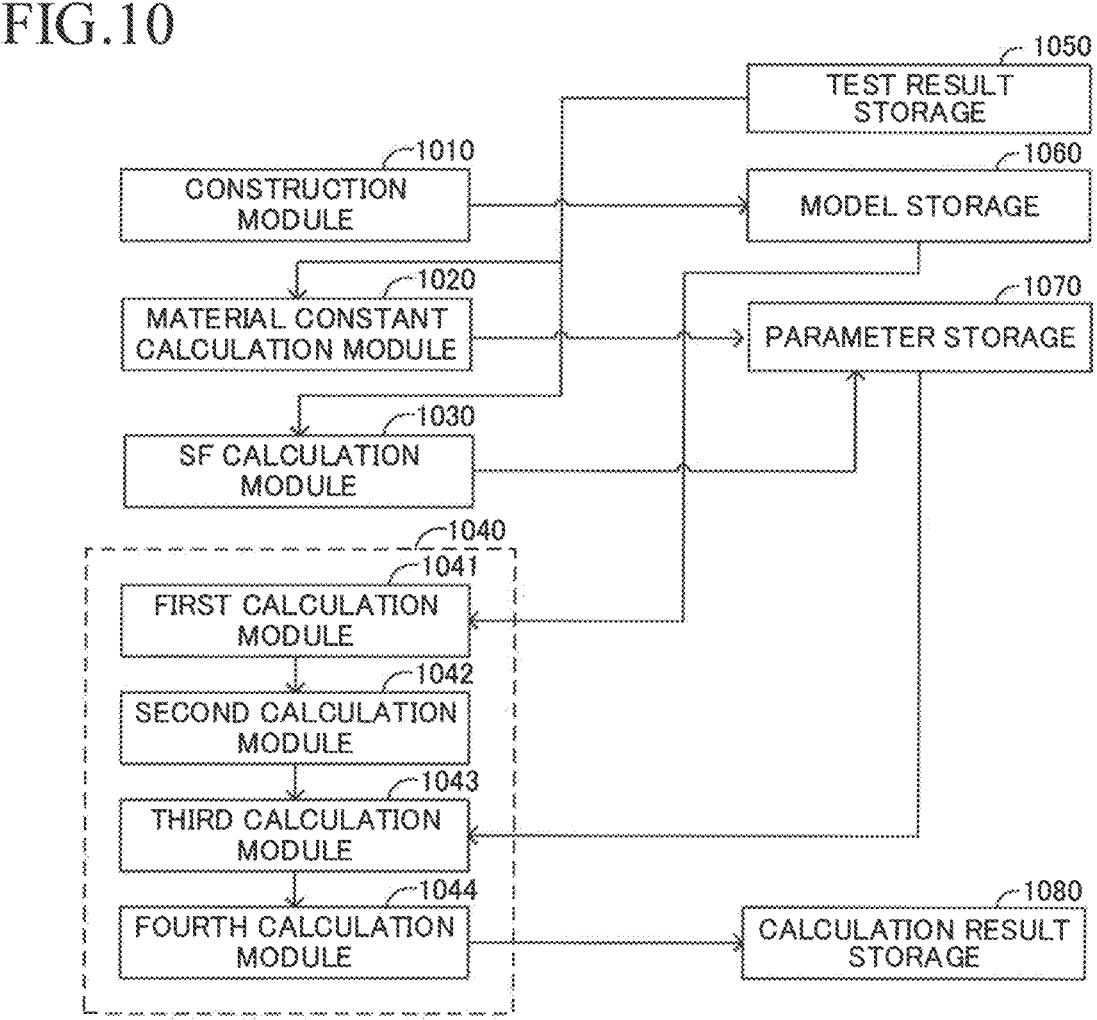
FIG. 10 is a block diagram for illustrating the function configuration of the analysis apparatus according to the embodiment of the present disclosure.

The CPU 911 is configured to read out and execute the instruction stored in the ROM 913 to achieve the respective functions of "a construction module 1010, a material constant calculation module 1020, a shift factor (SF) calculation module 1030, and a stress calculation module 1040" illustrated in FIG. 10. "A test result storage 1050, a model storage 1060, a parameter storage 1070, and a calculation result storage 1080" illustrated in FIG. 10 are achieved by the RAM 912 and/or the HDD 914.

The construction module 1010 constructs the viscoelastic material model of the viscoelastic material to be used as an analysis object. In the viscoelastic material model the viscoelastic material serving as an analysis object is represented as an aggregate of an element and a node (grid point). For example, when the viscoelastic material is represented by using a two-dimensional model, a triangular element having three nodes or a quadrangular element having four nodes is used as each element. When the viscoelastic material is represented by using a three-dimensional model, a tetrahedral element or a hexahedral element may be used as each element. In the viscoelastic material model, node coordinate values in a coordinate system, an element shape, material characteristics, and the like are defined for each element. The construction module 1010 can be achieved by using, for example, general-purpose software based on a known technology called a preprocessor. The construction module 1010 stores in the model storage 1060 the viscoelastic material model divided into a finite number of elements each having nodes.

The test result storage 1050 stores data on test results (e.g., the results of a harmonic oscillation test and a stress relaxation test) required for the calculation of the material constants $m_i$ and $A_i$, the rigidity ratios $\gamma_0$ and $\gamma_i$, the superelastic coefficients C10, C20, and C30 in the elastic element, and the shift factor $\alpha(T)$.

The material constant calculation module 1020 acquires the data on the test results from the test result storage 1050 to calculate the material constants $m_i$ and $A_i$, and rigidity ratios $\gamma_0$ and $\gamma_i$ of the viscoelastic material model, and the superelastic coefficients C10, C20, and C30 in the elastic element (those values are hereinafter sometimes collectively referred to as "parameters") as described above. The material constant calculation module 1020 stores the calculated parameters in the parameter storage 1070. In order to enable the analysis of a plurality of kinds of viscoelastic materials, the parameter storage 1070 may store the parameters for each viscoelastic material.

The SF calculation module 1030 acquires data on the test results of the harmonic oscillation test performed at a plurality of environmental temperatures from the test result storage 1050. The SF calculation module 1030 calculates the elastic modulus G(T) at each of the plurality of environmental temperatures. Next, the SF calculation module 1030 normalizes the elastic modulus G(T) at each of the plurality of environmental temperatures through the use of the reference elastic modulus $G(T_0)$ at the reference temperature $T_0$ out of the plurality of environmental temperatures. The SF calculation module 1030 determines the function f(T) representing a relationship between the logarithmic value log $(G(T)/G(T_0))$ of the normalized elastic modulus and the temperature T as shown in FIG. 8B. The SF calculation module 1030 calculates the shift factor $\alpha(T)$ on the basis of the material constant $m_i$, the function f(T), and the relationship represented by the expression (30). The SF calculation module 1030 stores the calculated shift factor $\alpha(T)$ in the parameter storage 1070. In order to enable the analysis of a plurality of kinds of viscoelastic materials, the parameter storage 1070 may store the shift factor $\alpha(T)$ for each viscoelastic material.

The stress calculation module 1040 calculates a displacement amount, a strain amount, and a stress at a node of each element through the use of the viscoelastic material model. The stress calculation module 1040 has a first calculation module 1041, a second calculation module 1042, a third calculation module 1043, and a fourth calculation module 1044.

The first calculation module 1041 acquires the viscoelastic material model from the model storage 1060. The first calculation module 1041 sets boundary conditions for the viscoelastic material model to calculate a displacement amount U of a node hi each element from an input condition for each calculation step. The boundary conditions are various conditions to be given to the viscoelastic material model at the time of the simulation of the behavior of the viscoelastic material. The first calculation module 1041 produces a rigidity matrix for solving a rigidity equation in each element. Then, the first calculation module 1041 produces an entire rigidity matrix representing the entire structure of the viscoelastic material model. The first calculation module 1041 introduces input conditions (e.g., the displacement amount of a known node and node force of the known node) into the entire rigidity matrix to execute analysis processing, to thereby calculate the displacement amount U of an unknown node. The first calculation module 1041 can be achieved by using, for example, general-purpose software based on a known technology called a solver.

The second calculation module 1042 receives the displacement amount U obtained by the first calculation module 1041 as an input value. The second calculation module 1042 calculates a strain rate at each node of each element through the use of the displacement amount U. The second calculation module 1042 calculates a strain rate in the step n+1 serving as the next calculation step through the use of a strain amount obtained in the calculation step n.

The second calculation module 1042 calculates a total displacement amount $\varphi_{n+1}$ in the calculation step n+1 from a total displacement amount $\varphi_n$ of the nodes in the calculation step n and the displacement amount U obtained by the first calculation module 1041 in accordance with an expression "$\varphi_{n+1}=\varphi_n+U$". Here, relationships represented by the following expression (31) to the expression (36) are valid.

$$\varphi_{n+1}=\varphi_n+U \quad (31)$$

$$F_{n+1}=D\varphi_{n+1} \quad (32)$$

$$J_{n+1}=\det[F_{n+1}] \quad (33)$$

$$C_{n+1}=F_{n+1}^T F_{n+1} \quad (34)$$

$$\overline{F}_{n+1}=J_{n+1}^{-1/3}F_{n+1} \quad (35)$$

$$\overline{C}_{n+1}=J_{n+1}^{-2/3}C_{n+1} \quad (36)$$

The second calculation module 1042 calculates, from the total displacement amount $\varphi_{n+1}$, and the relationships represented by the expression (32) to the expression (36), a deformation gradient tensor $F_{n+1}$, a volume change ratio (Jacobian) $J_{n+1}$, a right Cauchy-Green tensor $C_{n+1}$, a modified deformation gradient tensor
$\overline{F}_{n+1}$
from which a deviator has been removed, and a modified right Cauchy-Green tensor
$\overline{C}_{n+1}$
in the calculation step n+1.

D in the expression (32) is a differential operator for obtaining the deformation gradient tensor F.

The second calculation module 1042 calculates, from the modified right Cauchy-Green tensor obtained by the expression (36) and the strain amount in the calculation step n, a strain amount and a strain rate in the calculation step n+1 in accordance with the following expression (37) and expression (38). $\Delta t_n$ represents a time step discretized in correspondence with each calculation step.

$$\overline{E}_{n+1} = \frac{1}{2}(\overline{C}_{n+1} - I) \quad (37)$$

-continued $$\overline{E}'_{n+1} = \frac{\overline{E}_{n+1} - \overline{E}_n}{\Delta t_n} \qquad (38)$$

The third calculation module 1043 receives the strain rate obtained by the second calculation module 1042 as an input value. Further, the third calculation module 1043 acquires the material constants $m_i$ and $A_i$ from the parameter storage 1070. Further, the third calculation module 1043 acquires the shift factor $\alpha(T)$ corresponding to the environmental temperature T from the parameter storage 1070. The third calculation module 1043 calculates the relaxation time required for the calculation of a stress from the material constants $m_i$ and $A_i$, the shift factor $\alpha(T)$, and the strain rate. Specifically, the third calculation module 1043 calculates the relaxation time $\tau_i$ from the expression (23) and the expression (24).

The fourth calculation module 1044 receives the relaxation time $\tau_i$ obtained by the third calculation module 1043 as an input value. The fourth calculation module 1044 determines a Kirchhoff stress at a node with the relaxation time $\tau_i$. First, the fourth calculation module 1044 determines the Kirchhoff elastic stress in the calculation step n+1 through the use of the expression (11). Next, the fourth calculation module 1044 determines the intermediate function $H^{(i)}_{n+1}$ through the use of the expression (20) and the expression (21), and determines
$\overline{S}_{n+1}^o$
through the use of the expression (12).

Next, the fourth calculation module 1044 calculates the Kirchhoff stress through the use of the expression (14) and the expression (22). The fourth calculation module 1044 stores in the calculation result storage 1080 the values of the intermediate function and the Kirchhoff stress obtained in each calculation step. The stress calculation module 1040 repeatedly executes the above-mentioned processing a predetermined number of calculation steps. Finally, the fourth calculation module 1044 produces a stress-strain curve and a stress relaxation curve in the viscoelastic material model from the calculation results stored in the calculation result storage 1080. The fourth calculation module 1044 causes the output device 930 to display the stress-strain curve and the stress relaxation curve.

<Operation>

Figure 11:
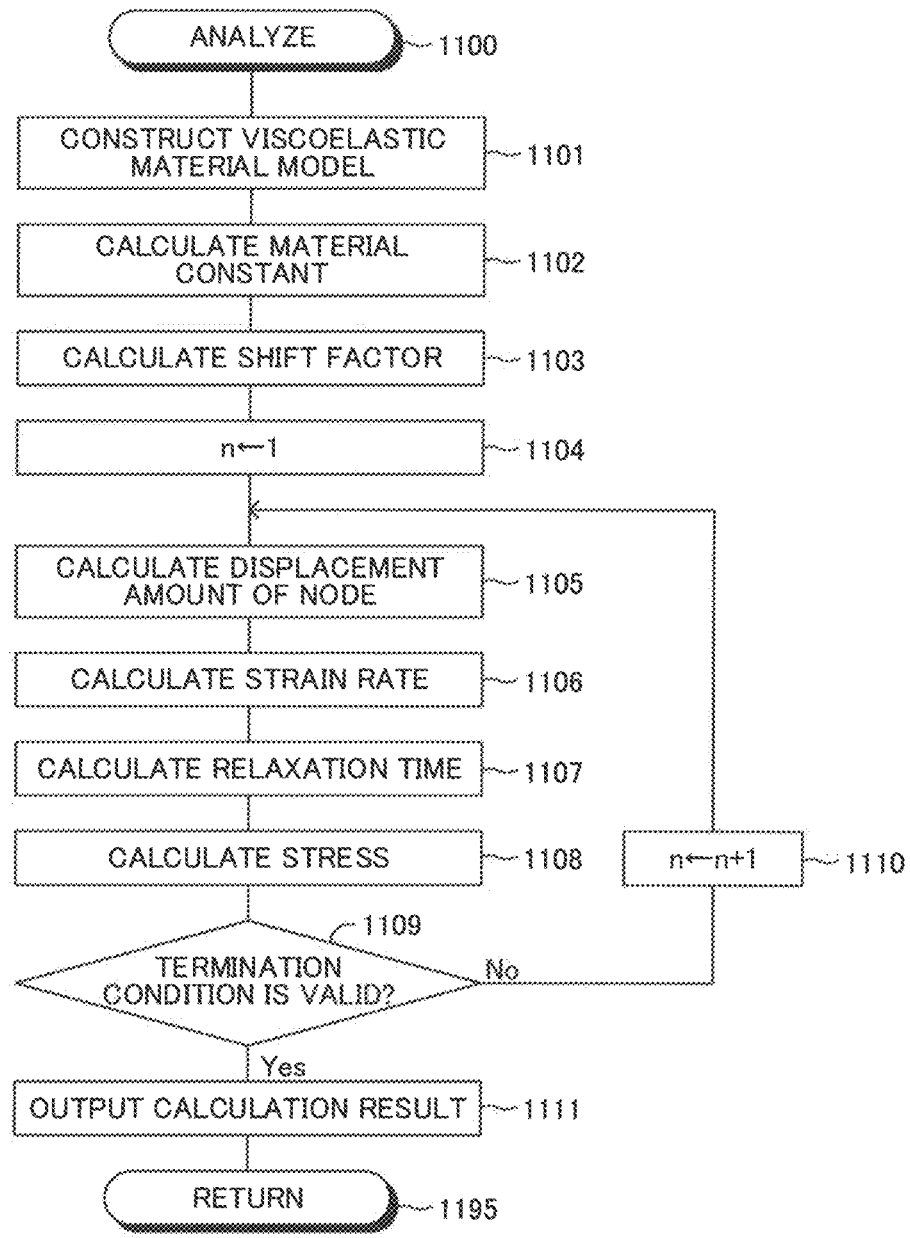
FIG. 11 is a flow chart for illustrating an "analysis routine" to be executed by a CPU in the embodiment of the present disclosure.

The CPU is configured to execute an "analysis routine" illustrated in FIG. 11 every time a predetermined time period elapses. At a predetermined timing, the CPU starts the routine illustrated in FIG. 11 from Step 1100 to execute processing in Step 1101 to Step 1108 below in order, and then proceeds to Step 1109.

Step 1101: The CPU constructs the viscoelastic material model of the viscoelastic material to be used as an analysis object.

Step 1102: The CPU calculates the material constants $m_i$ and $A_i$, and rigidity ratios $\gamma_0$ and $\gamma_i$ of the viscoelastic material model, and the superelastic coefficients C10, C20, and C30 in the elastic element as described above.

Step 1103: The CPU calculates the shift factor $\alpha(T)$ of the viscoelastic material model as described above.

Step 1104: The CPU sets the number of calculation steps n to "1".

Step 1105: The CPU calculates the displacement amount U at each node of each element of the viscoelastic material model as described above.

Step 1106: The CPU calculates the strain rate at the node of each element through the use of the displacement amount U as described above.

Step 1107: The CPU calculates the relaxation time $\tau_i$ from the material constants $m_i$ and $A_i$, the shift factor $\alpha(T)$, and the strain rate as described above.

Step 1108: The CPU calculates the Kirchhoff stress at the node through the use of the relaxation time $\tau_i$ as described above.

When the CPU proceeds to Step 1109, the CPU determines whether or not a predetermined termination condition is valid. The termination condition is valid when the processing in Step 1105 to Step 1108 described above is executed a predetermined number of calculation steps Nth, which has been determined in advance (i.e., when n=Nth).

When the termination condition is not valid, the CPU makes a determination "No" in Step 1109, and proceeds to Step 1110 to increment the number of calculation steps n. After that, the CPU returns to Step 1105.

When the termination condition is valid, the CPU makes a determination "Yes" in Step 1109, and proceeds to Step 1111. In Step 1111, the CPU produces the stress-strain curve and the stress relaxation curve in the viscoelastic material model from the calculation results, and causes the output device 930 to display the curves. After that, the CPU proceeds to Step 1195 to temporarily terminate the routine.

<Experimental Results>

Figure 12A:
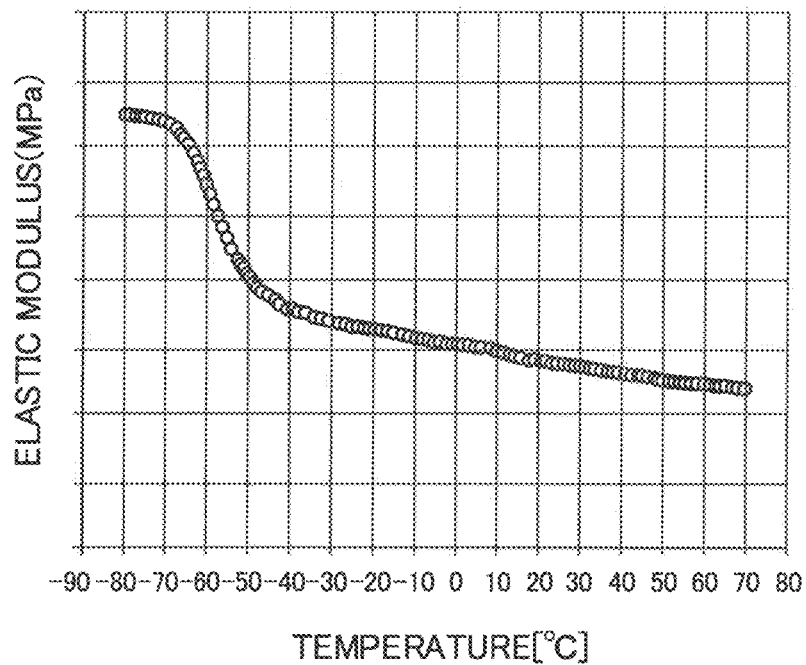
FIG. 12A is a graph for showing a relationship between a temperature and an elastic modulus at a time when a harmonic oscillation test is performed on a rubber material.
Figure 12B:
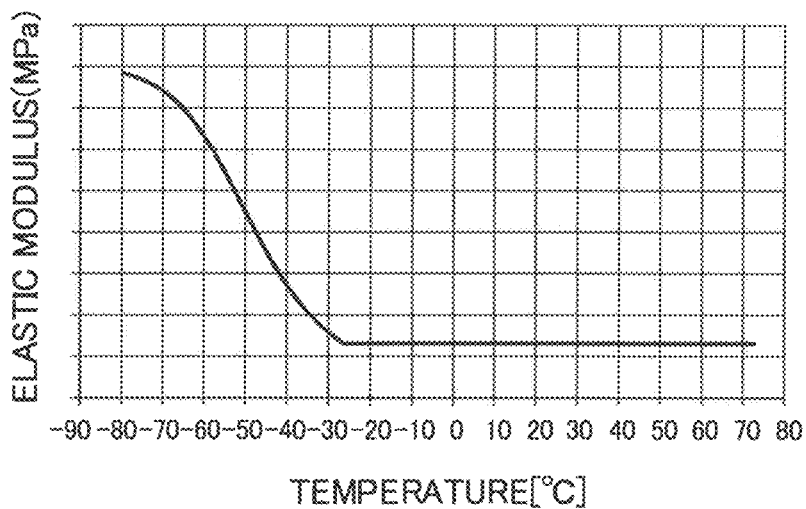
FIG. 12B is a graph for showing the result of the calculation of the relationship between the temperature and the elastic modulus with the analysis apparatus according to the embodiment of the present disclosure.

FIG. 12A is a graph for showing a relationship between a temperature and an elastic modulus at a time when a harmonic oscillation test is performed on a rubber material. Conditions for the harmonic oscillation test are as follows.
Amplitude: 0.2 μm
Frequency: 1 Hz
Prestrain: 0.25 N FIG. 12B is a graph for showing the result of the calculation of the relationship between the temperature and the elastic modulus in the analysis apparatus according to this embodiment. As shown in FIG. 12B, the analysis apparatus can reproduce the behavior of the elastic modulus of the rubber material with respect to a change in environmental temperature.

Figure 13A:
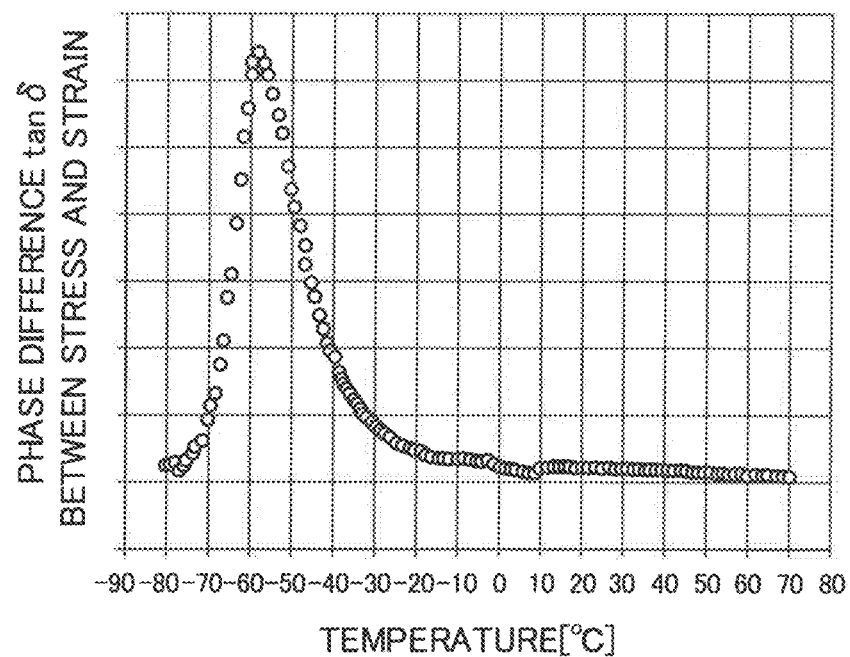
FIG. 13A is a graph for showing a relationship between a "temperature" and a "phase difference between a stress and a strain" at a time when a harmonic oscillation test is performed on a rubber material.
Figure 13B:
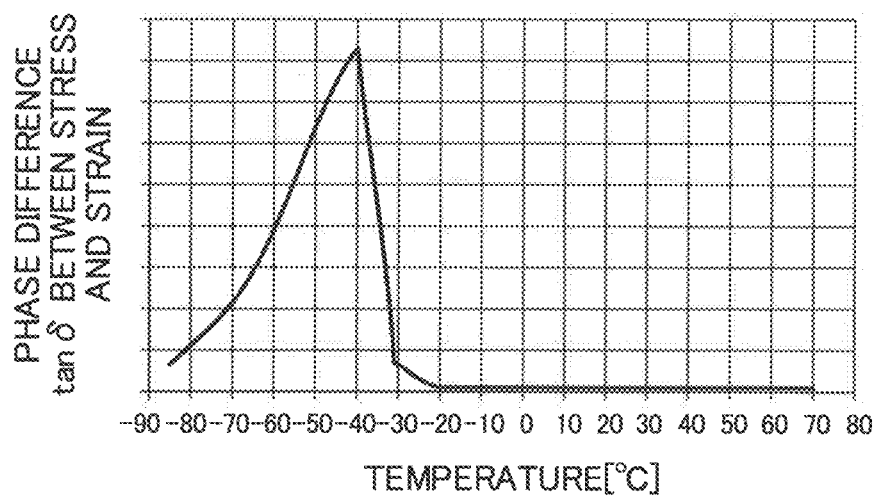
FIG. 13B is a graph for showing the result of the calculation of the relationship between the "temperature" and the "phase difference between the stress and the strain" with the analysis apparatus according to the embodiment of the present disclosure.

FIG. 13A is a graph for showing a relationship between a "temperature" and a "phase difference tan δ between a stress and a strain" at a time when a harmonic oscillation test is performed under the same conditions as those described above. FIG. 13B is a graph for showing the result of the calculation of the relationship between the "temperature" and the "phase difference tan δ between the stress and the strain" in the analysis apparatus according to this embodiment. The analysis apparatus can also reproduce the behavior of the "phase difference between the stress and the strain" with respect to a change in environmental temperature.

In the analysis apparatus according to this embodiment, the relaxation time $\tau_i$ representing the damping characteristics of a viscoelastic element is defined as a power function of the shift factor of the temperature-time conversion law. Therefore, the analysis apparatus can reproduce the dependence of a viscoelastic material on an environmental temperature. Thus, the accuracy with which the characteristics (e.g., stress-strain characteristics) of the viscoelastic material are predicted can be improved.

The present disclosure is not limited to the embodiment described above, and various modification examples can be adopted within the scope of the present disclosure.

The method of calculating the shift factor $\alpha(T)$ of the temperature-time conversion law is not limited to the above-mentioned example. The SF calculation module 1030 may determine the shift factor α(T) in accordance with the following flow. For example, a stress relaxation test is performed on the test body of the viscoelastic material at a plurality of environmental temperatures (T=$T_0$, $T_1$, $T_2$, ..., $T_N$). At this time, a prestrain is constant, and a strain rate is also constant.

Figure 14A:
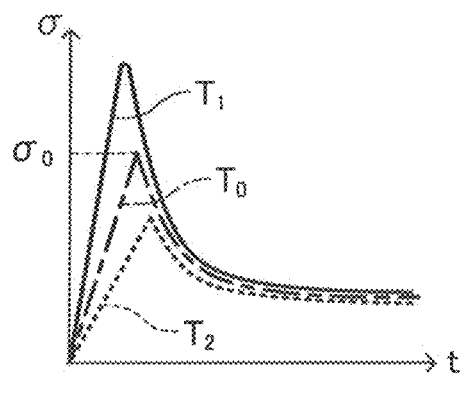
FIG. 14A, FIG. 14B, FIG. 14C, and FIG. 14D are each a graph for showing the flow of the calculation of the shift factor of a temperature-time conversion law in a modification example of the present disclosure.
Figure 14B:
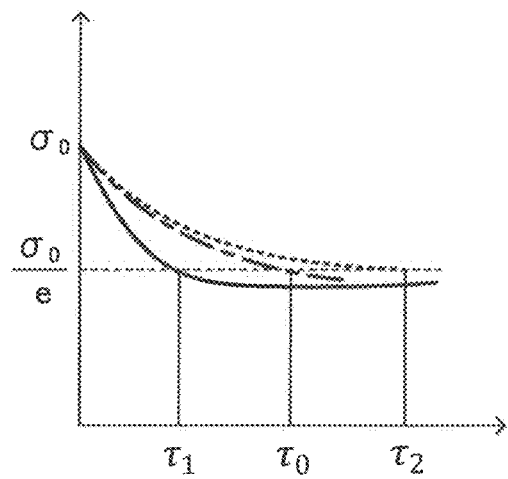

As shown in FIG. 14A, the SF calculation module 1030 produces, from data on the test results of the stress relaxation test, a stress relaxation graph for each of the plurality of environmental temperatures. In this case, the temperature $T_0$ out of the plurality of environmental temperatures is used as a reference temperature. Next, the SF calculation module 1030 normalizes the stress relaxation graph for each of the plurality of environmental temperatures through the use of a maximum stress $\sigma_0$ at the reference temperature $T_0$. Then, as shown in FIG. 14B, the SF calculation module 1030 calculates a relaxation time ($T_0$, $T_1$, $T_2$, ...) at each of the plurality of environmental temperatures.

Figure 14C:
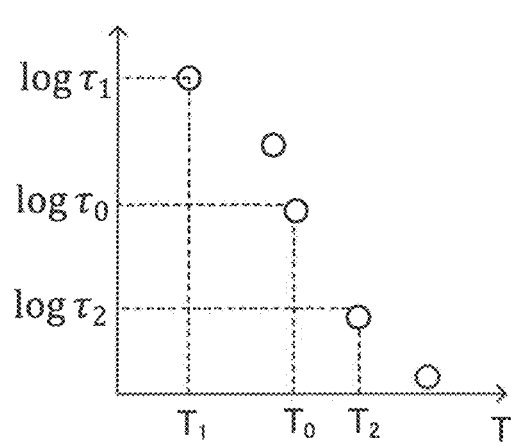
Figure 14D:
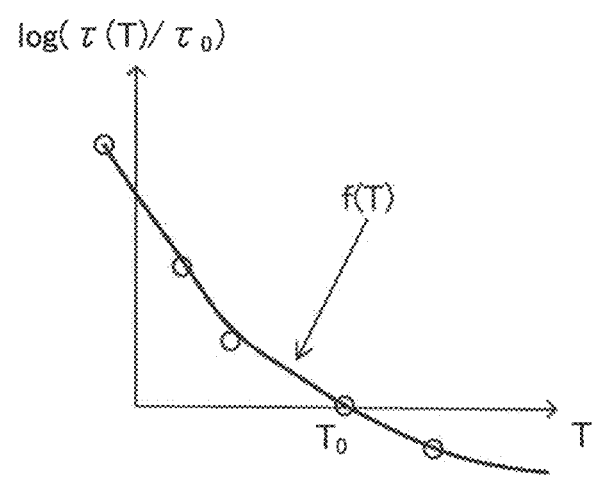

Next, as shown in FIG. 14C, the SF calculation module 1030 produces a graph for showing a relationship between the logarithmic value of the relaxation time and the temperature. Next, the SF calculation module 1030 normalizes the logarithmic value of the relaxation time at each of the plurality of environmental temperatures through the use of the relaxation time $T_0$ at the reference temperature $T_0$. Then, as shown in FIG. 14D, the SF calculation module 1030 produces a scatter diagram in which a "normalized logarithmic value $\log(\tau(T)/\tau_0)$ of the relaxation time" is plotted against an axis of abscissa indicating the temperature T. The SF calculation module 1030 determines a regression function f(T) in accordance with the method of least squares. The regression function f(T) may be any one of a regression line and a regression curve. The expression (30) is valid for a relationship between the determined function f(T) and the shift factor α(T). Therefore, the SF calculation module 1030 calculates the shift factor α(T) on the basis of the material constant $m_i$, the function f(T), and the relationship represented by the expression (30). The SF calculation module 1030 stores the calculated shift factor α(T) in the parameter storage 1070.

The material constant $A_i$ may be calculated from the results of the constant strain rate test. The deformation of the expression (28) provides the following expression (39).

$$A_i = \frac{(\bar{\omega}_i \varepsilon)^{1+m_i}}{\varepsilon} \quad (39)$$

$\bar{\omega}_i \varepsilon$ in the numerator of the expression (39) represents the maximum strain rate in the harmonic oscillation test, and hence can be associated with a strain rate $V_{nom}$ in the constant strain rate test. In addition, the amplitude ε in the denominator of the expression (39) represents the maximum strain amount in the harmonic oscillation test, and hence can be associated with a measured strain E* in the constant strain rate test. Therefore, the expression (39) can be rewritten into the following expression (40) by using the strain rate $V_{nom}$ and the measured strain E* in the constant strain rate test.

$$A_i = \frac{V_{nom}^{1+m_i}}{E_*} \quad (40)$$

Therefore, the material constant $A_i$ can be calculated from the test results in the constant strain rate test by using the expression (40).

What is claimed is:

1. An analysis apparatus, comprising:
   a non-transitory computer readable medium, wherein the non-transitory computer readable medium is configured to:
      store instructions; and
      receive test results from a harmonic oscillation test performed on a viscoelastic material based on a viscoelastic material constitutive law in which an elastic element and a viscoelastic element are arranged in parallel with each other; and
   a processor connected to the non-transitory computer readable medium, wherein the process is configured to execute the instructions to function as:
      a first calculation module configured to set a predetermined input condition for a viscoelastic material model divided into a finite number of elements each having a node to calculate a displacement amount of the node;
      a second calculation module configured to calculate a strain rate at the node through use of the displacement amount;
      a third calculation module configured to calculate, as a relaxation time of the viscoelastic element, a value proportional to a value of a power using the strain rate as a base and a value of a power using a shift factor of a temperature-time conversion law as a base; and
      a fourth calculation module configured to calculate a stress at the node through use of the relaxation time.

2. An analysis apparatus according to claim 1, wherein the processor is further configured to execute the instructions to function as a shift factor calculation module configured to calculate the shift factor,
   wherein the shift factor calculation module is configured to:
      calculate, from test results of a harmonic oscillation test performed at a plurality of environmental temperatures by using the viscoelastic material serving as an analysis object, an elastic modulus of the viscoelastic material at each of the plurality of environmental temperatures;
      normalize the elastic modulus at each of the plurality of environmental temperatures through use of a reference elastic modulus at a reference temperature out of the plurality of environmental temperatures;
      determine a function f(T) representing a relationship between a logarithmic value of the normalized elastic modulus and a temperature; and
      calculate a shift factor α(T) based on a material constant $m_i$ obtained from a relationship between an elastic modulus and an amplitude in the harmonic oscillation test in which the viscoelastic material is used, the function f(T), and the following expression (A)

$$f(T) = (1+m_i)\log \alpha(T) \quad (A).$$

3. An analysis apparatus according to claim 1, wherein the processor is further configured to execute the instructions to function as a shift factor calculation module configured to calculate the shift factor, wherein the shift factor calculation module is configured to:
- produce, from test results of a stress relaxation test performed at a plurality of environmental temperatures by using the viscoelastic material serving as an analysis object, a stress relaxation graph for each of the plurality of environmental temperatures;
- normalize the stress relaxation graph for each of the plurality of environmental temperatures through use of a maximum stress at a reference temperature out of the plurality of environmental temperatures to calculate a relaxation time at each of the plurality of environmental temperatures;
- normalize a logarithmic value of the relaxation time at each of the plurality of environmental temperatures through use of a relaxation time at the reference temperature to determine a function f(T) representing a relationship between the normalized logarithmic value of the relaxation time and a temperature; and
- calculate a shift factor α(T) based on a material constant $m_i$ obtained from a relationship between an elastic modulus and an amplitude in a harmonic oscillation test in which the viscoelastic material is used, the function f(T), and the following expression (B)

$$f(T)=(1+m_i)\log \alpha(T) \quad \text{(B)}.$$

4. An analysis apparatus according to claim 1, wherein an exponent of the value of the power using the shift factor as a base is a value obtained by adding 1 to an exponent of the value of the power using the strain rate as a base.

5. A method of determining characteristics of a viscoelastic material based on a viscoelastic material constitutive law in which an elastic element and a viscoelastic element are arranged in parallel with each other, the method comprising:
- performing a harmonic oscillation test on the viscoelastic material; and
- setting a predetermined input condition for a viscoelastic material model divided into a finite number of elements each having a node;
- calculating a displacement amount of the node;
- calculating a strain rate at the node through use of the displacement amount;
- calculating, as a relaxation time of the viscoelastic element, a value proportional to a value of a power using the strain rate as a base and a value of a power using a shift factor of a temperature-time conversion law as a base; and
- calculating a stress at the node through use of the relaxation time.

6. The method according to claim 5, further comprising determining whether the stress at the node is calculated for a threshold number of nodes.

7. The method according to claim 6, further comprising repeating, in response to a determination that the threshold number of nodes is not satisfied, the calculating the displacement amount, the calculating the strain rate, the calculating the value, and the calculating the stress for a second node of a different element of the finite number of elements.

8. The method according to claim 7, further comprising generating, in response to a determination that the threshold number of notes is satisfied, a stress-strain curve for the viscoelastic material.

9. The method according to claim 8, further comprising displaying the generated stress-strain curve to a user.

10. The method according to claim 9, further comprising pausing for a predetermined time period following the displaying of the generated stress-strain curve.

11. The method according to claim 10, further comprising repeating the calculating the displacement amount, the calculating the strain rate, the calculating the value, and the calculating the stress after the predetermined time period has elapsed.

12. The method according to claim 5, further comprising repeating the calculating the displacement amount, the calculating the strain rate, the calculating the value, and the calculating the stress after the predetermined time period has elapsed.

* * * * *